US005837523A

United States Patent [19]
Greene et al.

[11] Patent Number: 5,837,523
[45] Date of Patent: Nov. 17, 1998

[54] COMPOSITIONS AND METHODS OF TREATING TUMORS

[75] Inventors: Mark I. Greene, Penn Valley; Xiaolan Qian, Philadelphia, both of Pa.

[73] Assignee: The Trustees of the University of Pennsylvania, Philadelphia, Pa.

[21] Appl. No.: 737,269
[22] PCT Filed: May 5, 1995
[86] PCT No.: PCT/US95/05614
  § 371 Date: Feb. 11, 1997
  § 102(e) Date: Feb. 11, 1997
[87] PCT Pub. No.: WO95/30331
  PCT Pub. Date: Nov. 16, 1995

Related U.S. Application Data

[63] Continuation-in-part of Ser. No. 239,202, May 5, 1994, abandoned.
[51] Int. Cl.⁶ .............................. C12N 15/00; C07H 21/02
[52] U.S. Cl. ......................... 435/320.1; 536/23.5; 935/10
[58] Field of Search .................................. 536/23.1, 23.5; 435/320.1, 172.3; 514/44; 935/10

[56] References Cited

U.S. PATENT DOCUMENTS 5,108,921   4/1992   Low et al. ............................ 435/240.1

OTHER PUBLICATIONS

Akiyama et al., "The Product of the Human c–erbB–2 Gene: A 185–Kilodalton Glycoprotein with Tyrosine Kinase Activity", *Science*, 1986, 232, 1644–1646.
Anderson et al, "Potocytosis, Sequestration and Transport of Small Molecules by Caveolae", *Science*, 1992, 255, 410–411.
Antony, "The Biological Chemistry of Folate Receptors", *Blood*, 1992, 79(11), 2807–2820.
Bargmann et al., "The NeU Oncogene Encodes an Epidermal Growth Factor Receptor–Related Protein", *Nature*, 1986, 319, 226–230.
Bargmann et al., "Oncogenic Activation of the Neu–Encoded Receptor Protein by point Mutation and Deletion", *EMBO J.*, 1988, 7, 2043–2052.
Bargmann et al., "Multiple Independent Activations of the Neu Oncogene by a Point Mutation Altering the Transmembrane Domain of p185", *Cell*, 1986, 45, 649–657.
Bargmann et al., "Increased Tyrosine Kinase Activity Associated with the Protein Encoded by the Activated Neu Oncogene", *Proc. Natl. Acad. Sci. USA*, 1988, 85, 5394–5398.
Böni–Schnetzler et al., "Ligand–Dependent Intersubunit Association within the Insulin Receptor Complex Activates its Intrinsic Kinase Activity", *J. Biol. Chem.*, 1988, 263, 6822–6828.
Chazin et al., "Transformation Mediated by the Human HER–2 Gene Independent of the Epidermal Growth Factor Receptor", *Oncogene*, 1992, 7, 1859–1866.

Chen et al., "Functional Independence of the Epidermal Growth Factor Receptor from a Domain Required for a Ligand–Induced Internalization and Calcium Regulation", *Cell*, 1989, 59, 33–43.
Chou et al., "Human Insulin Receptors Mutated at the ATP–binding Site Lack Protein Tyrosine Kinase Activity and Fail to Mediate Postreceptor Effects of Insulin", *J. Biol. Chem.*, 1987, 262, 1842–1847.
Clarenc et al., "Delivery of Antisense Oligonucleotides by Poly(L–Lysine) Conjugation and Lipsome Encapsulation", *Anti–Cancer Drug Design*, 1993, 8, 81–94.
Connelly and Stern, "The Epidermal Growth Factor Receptor and the Product of the Neu Protoncogene are Members of a Receptor Tyrosine Phosphorylation Cascade", *Proc. Natl. Acad. Sci. USA*, 1990, 87, 6054–6057.
Cooper and MacAuley, "Potential Positive and Negative Autoregulation of p60$^{c-src}$ by Intermolecular autophosphorylation", *Proc. Natl. Acad. Sci. USA*, 1988, 85, 4232–4236.
Cotten et al., "High–Efficiency Receptor–Mediated Delivery of Small and large (48 Kilobase Gene Constructs Using the Endosome–Disruption Activity of Defective or Chemically Inactivated Adenovirus Particles", *Proc. Natl. Acad. Sci. USA*, 1992, 89, 6094–6098.
Culver et al., "Gene therapy for cancer", *Trends in Genetics*, 1994, 10(5), 174–178.
Curiel et al., "Gene Transfer to Respiratory Epithelial Cells Via the Receptor–Mediated Endocytosis Pathway", *Am. J. Respir. Cell Mol. Bio.*, 1992, 6, 247–252.
Curiel et al., "Adenovirus Enhancement of Transferrin–Polylysine–Mediated Gene Delivery", *Proc. Natl. Acad. Sci. USA*, 1991, 88, 8850–8854.
Daniel et al., "Purification of the Platelet–Derived Growth Factor Receptor by using an Anti–Phosphotyrosine Antibody", *Proc. Natl. Acad. Sci. USA*, 1985, 82, 2684–2687.
DiFiore et al., "erbB–2 Is a Potent Oncogene When Overexpressed in NIH/3T3 Cells", *Science*, 1987, 237, 178–182.
DiFiore et al., "Overexpression of the Human EGF Receptor Confers an EGF–Dependent Transformed Phenotype to NIH 3T3 Cells", *Cell*, 1987, 51, 1063–1070.
DiMarco et al., "Transformation of NIH 3T3 Cells by Overexpression of the Normal Coding Sequence of the Rat Neu Gene", *Mol. Cell. Biol.*, 1990, 10, 3247–3252.
Dobashi et al., "Characterization of a Neu/C–ErbB–2 Protein–Specific Activating Factor", *Proc. Natl. Acad. Sci. USA*, 1991, 88, 8582–8586.
Dougall et al., "Interaction of the Neu/p185 and EGF Receptor Tyrosine Kianses: Implications for Cellular Transformation and Tumor Therapy", *J. Cell Biochem.*, 1993, 53, 61–73.

(List continued on next page.)

*Primary Examiner*—Bruce R. Campell
*Attorney, Agent, or Firm*—Woodcock Washburn Kurtz Mackiewicz & Norris, LLP

[57] ABSTRACT

Nucleic acid molecules that comprise a nucleotide sequence that encodes a protein that dimerizes with epidermal growth factor receptor and p185 and lacks tyrosine kinase activity are disclosed. The nucleic acid molecules in combination with delivery components are disclosed.

29 Claims, No Drawings

OTHER PUBLICATIONS

Drebin et al., "Down–Modulation of an Oncogene Protein Product and Reversion of the Transformed Phenotype by Monoclonal Antibodies", *Cell,* 1985, 41, 695–706.

Felder et al., "Kinase Activity Controls the Sorting of the Epidermal Growth Factor Receptor Within the Multivascular Body", *Cell,* 1990, 61, 623–634.

Gaulton et al., "Interleukin 2–Dependent Phosphorylation of Interleukin 2 Receptors and Other T Cell Membrane Proteins", *J. Immunol.,* 1986, 7, 2470–2477.

Goldman et al., "Heterodimerization of the erbB–1 and erbB–s Receptors in Human Breast Carcinoma Cells: A Mechanism for Receptor Transregulation", *Biochem.,* 1990, 29, 11024–11028.

Gorman et al., "Growth Factors and Their Receptors: Genetic Control and Rational Application", *J. Cell. Biochem.,* 1988, 12A Suppl. C219, 104.

Hernandez–Sotomayer et al., "Epidermal Growth Factor Receptor: Elements of Intracellular Communication", *J. Membrane Biol.,* 1992, 128, 81–89.

Hodgson, "Advances in vector systems for gene therapy", *Exp. Opin. Ther. Patents,* 1995, 5(5), 459–568.

Honegger et al., "Separate Endocytic Pathways of Kinase–Defective and –Active EGF Receptor Mutants Expressed in Same Cells", *J. Cell. Biol.,* 1990, 110, 1541–1548.

Honegger et al., "Point Mutation at the ATP Binding Site of EGF Receptor Abolishes Protein–Tyrosine Kinase Activity and Alters Cellular Routing", *Cell,* 1987, 51, 199–209.

Honegger et al., "Evidence for Epidermal Growth Factor (EGF)–Induced Intermolecular Autophosphorylation of the EGF Receptors in Living Cells", *Mol. Cell. Biol.,* 1990, 10, 4035–4044.

Hung et al., "Amplification of the Proto–Neu Oncogene Facilitates Oncogenic Activation by a Single Point Mutation", *Proc. Natl. Acad. Sci. USA,* 1989, 86, 2545–2548.

Kashles et al., "A Dominant Negative Mutation Suppresses the Function of Normal Epidermal Growth Factor Receptors by Heterodimerization", *Mol. Cell. Biol.,* 1991, 11, 1454–1463.

Kern et al., "p185$^{neu}$ Expression in Human Lung Adenocarcinomas Predicts Shortened Survival", *Cancer Res.,* 1990, 50, 5184–5191.

King et al., "EGF Binding to its Receptor Triggers a Rapid Tyrosine Phosphorylation of the erbB–2 Protein in the Mammary Tumor Cell Line SK–BR–3", *EMBO J.,* 1988, 7, 1647–1651.

Kokai et al., "Phosphorylation Process Induced by Epidermal Growth Factor Alters the Oncogenic and Cellular Neu (NGL) Gene Products", *Proc. Natl. Acad. Sci. USA,* 1988, 85, 5389–5393.

Kokai et al., "Stage–and Tissue–Specific Expression of the neu Oncogene in Rat Development", *Proc. Natl. Acad. Sci. USA,* 1987, 84, 8498–8501.

Kokai et al., "Synergistic Interaction of p185c–neu and the EGF Receptor Leads to Transformation of Rodent Fibroblasts", *Cell,* 1989, 58, 287–292.

Kornilova et al., "Surface Expression of erbB–2 Protein is Post–Transcriptionally Regulated in Mammary Epithelial Cells by Epidermal Growth Factor and by the Culture Density", *Oncogene,* 1992, 7, 511–519.

Laemmli, "Cleavage of Structural Proteins during the Assembly of the Head of Bacteriophage T4", *Nature,* 1970, 227, 680–686.

Leamon and Low, "Delivery of Macromolecules into Living Cells: A Method that Exploits Folate Receptor Endocytosis", *Proc. Natl. Acad. Sci. USA,* 88, 5572–5576.

Leamon and Low, "Cytotoxicity of Momordin–Folate Conjugated in Cultured Human Cells", *J. Bio. Chem.,* 1992, 267(35), 24966–24971.

Leamon and Low, "Membrane Folate–Binding Proteins are Responsible for Folate–Protein Conjugate Endocytosis Into Cultured Cells", *Biochem. J.,* 1993, 291, 855–860.

Lee and Low, "Delivery of Liposomes into Cultured KB Cells Via Folate Receptor–Mediated Endocytosis", *J. Biol. Chem.,* 1994, 269(5), 3198–3204.

Lofts et al., "Specific Short Transmembrane Sequences can Inhibit Transformation by the Mutant NEU Growth Factor Receptor in Vitro and in Vivo", *Oncogene,* 1993, 8, 2813–2820.

Marshall, "Gene Therapy's Growing Pains", *Science,* 1995, 269, 1050–1055.

McClain et al., "A Mutant Insulin Receptor with Defective Tyrosine Kinase Displays No Biologic Activity and Does Not Undergo Endocytosis", *J. Biol. Chem.,* 1987, 262, 14663–14671.

Miller et al., "Targeted vectors for gene therapy", *FASEB J.,* 1995, 9, 190–199.

Möller et al., "Phosphate–Binding Sequences in Nucleotide–Binding Proteins", *FEBS Lett.,* 1985, 186, 1–7.

Mori et al., "C–erbB–2 Gene Product, a Membrane Protein Commonly Expressed on Human Fetal Epithelial Cells", *Lab. Invest.,* 1989, 61, 93–97.

Papewalis et al., "G to A Polymorphism at Amino Acid Codon 655 of the Human erbB–2/HER2 Gene", *Nucl. Acids Res.,* 1991, 19, 5452.

Press et al., "Expression of the HER–2/neu proto–oncogene in Normal Human Adult and Fetal Tissues", *Oncogene,* 1990, 5, 953.

Pruss and Herschman, "Variants of 3T3 Cells Lacking Mitogenic Response to Epidermal Growth Factor", *Proc. Natl. Acad. Sci. USA,* 1977, 74, 3918–3921.

Qian et al., "p185$^{c-neu}$ and Epidermal Growth Factor Receptor Associate into a Structure Composed of Activated Kinases", *Proc. Natl. Acad. Sci. USA,* 1992, 89, 1330–1334.

Qian et al., "Heterodimerization of Epidermal Growth Factor Receptor and Wild–Type or Kinase–Deficient Neu: A Mechanism of Interreceptor Kinase Activation and Transphosphorylation", *Proc. Natl. Acad. Sci. USA,* 1994, 91, 1500–1504.

Qian et al., "Kinase–Deficient Neu Proteins Suppress Epidermal Growth Factor Receptor Function and Abolish Cell Transformation", *Oncogene,* 1994, 9, 1507–1514.

Rosenfeld et al., "Adenovirus–mediated transfer of a recombinant α1antitrypsin gene to the lung epithelium in vivo", *Science,* 1991, 252, 431–434.

Rudinger, J., "Characteristics of the amino acids as components of a peptide hormone sequence", *Peptide Hormones,* Parsons, J.A. (ed.), University Park Press, Baltimore, 1976, 1–7.

Russell et al., "The Protein–Tyrosine Kinase Activity of the Insulin Receptor is Necessary for Insulin–Mediated Receptor Down–Regulation", *J. Biol. Chem.,* 1987, 262, 11833–11840.

Salmons et al., "Targeting of retroviral vectors for gene therapy", *Human Gene Therapy,* 1993, 4, 129–141.

Schechter et al., "The Neu Oncogene: an erb–B–Related Gene Encoding a 185,000–M$_r$ Tumour Antigen", *Nature,* 1984, 312, 513–516.

Scott et al., "A Truncated Intracellular HER2/neu Receptor Produced by Alternative RNA Processing Affects Growth of Human Carcinoma Cells", *Mol. Cell. Biol.*, 1993, 13, 2247–2257.

Slamon et al., "Human Breast Cancer: Correlation of Relapse and Survival with Amplification of the HER–2/neu Oncogene", *Science*, 1987, 235, 177–182.

Slamon et al., "Studies of the HER–2/neu Proto–Oncogene in Human Breast and Ovarian Cancer", *Science*, 1989, 244, 707–712.

Southern et al., "Transformation of Mammalian Cells to Antibiotice Resistance with a Bacterial Gene Under Control of the SV40 Early Region Promoter", *J. Mol. Appl. Genet.*, 1982, 1, 327.

Spivak–Kroizman et al., "Heterodimerization of c–erbB2 with Different Epidermal Growth Factor Receptor Mutants Elicits Stimulatory or Inhibitory Responses", *J. Biol. Chem.*, 1992, 267, 8056–8063.

Sporn et al., "Peptide growth factors are multifunctional", *Nature*, 1988, 332, 217–219.

Sternberg et al., "Modelling the ATP–binding Site of Oncogene Products, the Epidermal Growth Factor Receptor and Related Proteins", *FEBS Lett.*, 1984, 175, 387–392.

Stern et al., "Oncogenic Activation of $p185^{neu}$ Stimulates Tyrosine Phosphorylation In Vivo", *Mol. Cell. Biol.*, 1988, 8, 3969–3973.

Takebe et al., "Srα Promoter: An Efficient and Versatile Mammalian cDNA Expression System Composed of the Simian Virus 40 Early Promoter and the R–U5 Segment of Human T–Cell Leukemia Virus Type 1 Long Terminal Repeat", *Mol. Cell. Biol.*, 1988, 8, 466–472.

Turek et al., "Endocytosis of Folate–Protein Conjugates: Ultrastructural Localization in KB Cells", *J. Cell Sci.*, 1993, 106, 423–430.

Wada et al., "Intermolecular Association of the $p185^{neu}$ Protein and EGF Receptor Modulates EGF Receptor Function", *Cell*, 1990, 61, 1339–1347.

Wagner et al., "Transferrin Receptor Mediated Gene Transfer", Serva Product Information, Catalog No. 70624, Transferring Infection Systems, Serva Feinbiochemica Kompoementar Gmbh, Heidelberg, Germany (2 pgs).

Wagner et al., "Transferrin–Polycation Conjugates as Carriers for DNA Uptake into Cells", *Proc. Natl. Acad. Sci. USA*, 1990, 87, 3410–3414.

Wagner et al., "DNA–Binding Transferrin Conjugates as Functional Gene–Delivery Agents: Synthesis by Linkage of Polylysine or Ethidium Homodimer to the Transferrin Carbohydrate Moiety", *Bioconjugate Chem.*, 1991, 2, 226–331.

Wagner et al., "Coupling of Adenovirus to Transferrin–Polylysine/DNA Complexes Greatly Enhances Receptor–Mediated Gene Delivery and Expression of Transfected Genes", *Proc. Natl. Acad. Sci. USA*, 1992, 89, 6099–6103.

Weiner et al., "Linkage of Tyrosine Kinase Activity with Transforming Ability of the p185neu Oncoprotein", *Oncogene*, 1989, 4, 1175–1183.

Weiner et al., "A Point Mutation in the Neu Oncogene Mimics Ligand Induction of Receptor Aggregation", *Nature*, 1989, 339, 230–231.

Wierenga et al., "Predicted Nucleotide–Binding Properties of p21 Protein and its Cancer–Associated Variant", *Nature*, 1983, 302, 842–843.

Williams et al., "Expression of c–erbB-2 in Human Pancreatic Adenocarcinomas", *Pathobiol.*, 1991, 59, 46–52.

Yamamoto et al., "Similarity of Protein Encoded by the Human c–erb–B–2 Gene to Epidermal Growth Factor Receptor", *Nature*, 1986, 319, 230–234.

Zenke et al., "Receptor–Mediated Endocytosis of Transferrin–Polycation Conjugates: An Efficient Way to Introduce DNA into Hematopoietic Cells", *Proc. Natl. Acad. Sci. USA*, 1990, 87, 3655–3659.

Zick et al., "Insulin–Like Growth Factor–I (IGF–I) Stimulates Tyrosine Kinase Activity in Purified Receptors from a Rat Liver Cell Line", *Biochem. Biophys. Res. Commun.*, 1984, 119, 6–13.

COMPOSITIONS AND METHODS OF TREATING TUMORS

CROSS REFERENCE TO RELATED APPLICATIONS

This application is the U.S. National Stage application of PCT International Application Number PCT/US95/05614 filed May 5, 1995, which is a continuation in part application of Ser. No. 08/239,202 filed May 5, 1994, abandoned.

FIELD OF THE INVENTION

The present invention relates to proteins which lack tyrosine kinase activity and dimerize with epidermal growth factor receptor and/or p185, to nucleic acid molecules that encode such proteins, to pharmaceutical compositions that comprise such nucleic acid molecules in combination with delivery vehicles which facilitate transfer of the nucleic acid molecule to a cell, and to methods of preventing tumors and treating individuals having tumors by administering such pharmaceutical compositions.

BACKGROUND OF THE INVENTION

The rat cellular protooncogene c-neu and its human counterpart c-erbB2 encode 185 kDa transmembrane glycoproteins termed p185. Tyrosine kinase (tk) activity has been linked to expression of the transforming phenotype of oncogenic p185 (Bargmann et al., *Proc. Natl. Acad. Sci. U.S.A.*, 1988, 85, 5394; and Stern et al., *Mol. Cell. Biol.*, 1988, 8, 3969, each of which is incorporated herein by reference). Oncogenic neu was initially identified in rat neuroglioblastomas (Schechter et al., *Nature*, 1984, 312, 513, which is incorporated herein by reference) and was found to be activated by a carcinogen-induced point mutation generating a single amino acid substitution, a Val to Glu substitution at position 664, in the transmembrane region of the transforming protein (Bargmann et al., *Cell*, 1986, 45, 649, which is incorporated herein by reference). This alteration results in constitutive activity of its intrinsic kinase and in malignant transformation of cells (Bargmann et al., *EMBO J.*, 1988, 7, 2043, which is incorporated herein by reference). The activation of the oncogenic p185 protein tyrosine kinase appears to be related to a shift in the molecular equilibrium from monomeric to dimeric forms (Weiner et al., *Nature*, 1989, 339, 230, which is incorporated herein by reference).

Overexpression of c-neu or c-erbB2 to levels 100-fold higher than normal (i.e., $>10^6$ receptors/cell) also results in the transformation of NIH3T3 cells (Chazin et al., *Oncogene*, 1992, 7, 1859; DiFiore et al., *Science*, 1987, 237, 178; and DiMarco et al., *Mol. Cell. Biol.*, 1990, 10, 3247, each of which is incorporated herein by reference). However, NIH3T3 cells or NR6 cells which express cellular p185 at the level of $10^5$ receptors/cell are not transformed (Hung et al., *Proc. Natl. Acad. Sci. U.S.A.*, 1989, 86, 2545; and Kokai et al., *Cell*, 1989, 58, 287, each of which is incorporated herein by reference), unless co-expressed with epidermal growth factor receptor (EGFR), a homologous tyrosine kinase (Kokai et al., *Cell*, 1989, 58, 287, which is incorporated herein by reference). Thus, cellular p185 and oncogenic p185 may both result in the transformation of cells.

Cellular p185 is highly homologous with EGFR (Schechter et al., *Nature*, 1984, 312, 513; and Yamamoto et al., *Nature*, 1986, 319, 230, each of which is incorporated herein by reference) but nonetheless is distinct. Numerous studies indicate that EGFR and cellular p185 are able to interact (Stern et al., *Mol. Cell. Biol.*, 1988, 8, 3969; King et al., *EMBO J.*, 1988, 7, 1647; Kokai et al., *Proc. Natl. Acad. Sci. U.S.A.*, 1988, 85, 5389; and Dougall et al., *J. Cell. Biochem.*, 1993, 53, 61; each of which is incorporated herein by reference). The intermolecular association of EGFR and cellular p185 appear to up-regulate EGFR function (Wada et al., *Cell*, 1990, 61, 1339, which is incorporated herein by reference). In addition, heterodimers which form active kinase complexes both in vivo and in vitro can be detected (Qian et al., *Proc. Natl. Acad. Sci. U.S.A.*, 1992, 89, 1330, which is incorporated herein by reference).

We have recently demonstrated that cellular rat p185 devoid of kinase activity due to either a single amino acid substitution in the consensus sequence for ATP binding, N757, or due to a cytoplasmic domain deletion, N691stop, was able to undergo EGF-induced heterodimerization with EGFR in living cells. EGF was also able to stimulate the transphosphorylation of N757 via EGFR. However, heterodimers composed of EGFR and certain truncated p185 proteins were kinase inactive. (See: Qian et al., *Proc. Natl. Acad. Sci. U.S.A.*, 1994, 91, 1500, which is incorporated herein by reference). Such structural alterations in receptors have been shown to act as dominant negative mutations that can suppress the function of wild type (wt) receptors, such as insulin receptor (Chou et al., *J. Biol. Chem.*, 1987, 262, 1842, which is incorporated herein by reference) or EGFR (Honegger et al., *J. Cell Biol.*, 1990, 110, 1541; and Kashles et al., *Mol. Cell. Biol.*, 1991, 11, 1454, each of which is incorporated herein by reference).

Cellular p185 proteins are found in adult secretory epithelial cells of the lung, salivary gland, breast, pancreas, ovary, gastrointestinal tract, and skin (Kokai et al., *Proc. Natl. Acad. Sci. U.S.A.*, 1987, 84, 8498; Mori et al., *Lab. Invest.*, 1989, 61, 93; and Press et al., *Oncogene*, 1990, 5, 953; each of which is incorporated herein by reference). Recent studies have found that the amplification of c-erbB2 occurs with high frequency in a number of human adenocarcinomas such as gastric (Akiyama et al., *Science*, 1986, 232, 1644, which is incorporated herein by reference), lung (Kern et al., *Cancer Res.*, 1990, 50, 5184, which is incorporated herein by reference) and pancreatic adenocarcinomas (Williams et al., *Pathobiol.*, 1991, 59, 46, which is incorporated herein by reference). It has also been reported that increased c-erbB2 expression in a subset of breast and ovarian carcinomas is linked to a less optimistic clinical prognosis (Slamon et al., *Science*, 1987, 235, 177; and Slamon et al., *Science*, 1989, 244, 707, each of which is incorporated herein by reference). Heterodimeric association of EGFR and p185 has also been detected in human breast cancer cell lines, such as SK-Br-3 (Goldman et al., *Biochemistry*, 1990, 29, 11024, which is incorporated herein by reference), and transfected cells (Spivak-Kroizman et al., *J. Biol. Chem.*, 1992, 267, 8056, which is incorporated herein by reference).

There is a need for therapeutic compositions useful to treat individuals identified as having p185-associated tumors. There is a need to develop prophylactic compositions for individuals susceptible to developing p185-associated tumors.

SUMMARY OF THE INVENTION

The present invention relates to nucleic acid molecules which comprise a nucleotide sequence that encodes a protein that lacks tyrosine kinase activity and dimerizes with EGFR or p185.

The present invention relates to nucleic acid molecules in combination with delivery components in which the nucleic acid molecules comprise a nucleotide sequence that encodes a protein that lacks tyrosine kinase activity and dimerizes with EGFR or p185.

The present invention relates to a pharmaceutical composition comprising a nucleic acid molecule in combination with delivery components. The nucleotide sequence of the nucleic acid molecule encodes a protein that lacks tyrosine kinase activity and dimerizes with human EGFR or human p185.

The present invention also relates to a method of treating an individual identified as undergoing p185-mediated cellular transformation. The treatment includes administering to the individual a pharmaceutical composition comprising a nucleic acid molecule in combination with delivery components in an amount sufficient to reverse the cellular transformation. The nucleic acid sequence encodes a protein that lacks tyrosine kinase activity and dimerizes with human EGFR or human p185.

The present invention also relates to a method of preventing p185-mediated cellular transformation in an individual identified as being susceptible to p185-mediated cellular transformation. A pharmaceutical composition comprising a nucleic acid molecule in combination with delivery components in an amount sufficient to prevent cellular transformation is administered to individuals at risk of p185 mediated tumors. The nucleic acid sequence encodes a protein that lacks tyrosine kinase activity and dimerizes with human EGFR or human p185.

DETAILED DESCRIPTION OF THE PREFERRED EMBODIMENTS

As used herein, the terms "neu-associated cancer" "neu-associated tumors" and "p185-associated tumors" are meant to refer to tumor cells and neoplasms which express the neu gene to produce p185.

As used herein, the term "delivery components" is meant to refer to vehicles by which nucleic acid molecules may be delivered to cells of an individual.

The present invention is useful to therapeutically treat an individual identified as suffering from neu-associated tumors in order to reverse the transformed phenotype of the tumor cells. The present invention is useful to prophylactically treat an individual who is predisposed to develop neu-associated tumors or who has had neu-associated tumors and is therefore susceptible to a relapse or recurrence.

As used herein, the term "high risk individual" is meant to refer to an individual who has had a neu-associated tumor either removed or enter remission and who is therefore susceptible to a relapse or recurrence. As part of a treatment regimen for a high risk individual, the individual can be prophylactically treated against the neu-associated tumors that they have been diagnosed as having had in order to combat a recurrence. Thus, once it is known that an individual has had cancer characterized by tumor cells with p185 on their cell surfaces, the individual can be treated according to the present invention to prevent normal cells from transforming into tumor cells.

The translation product of the neu oncogene is p185, a transmembrane glycoprotein having tyrosine kinase activity and a molecular weight of about 185,000 daltons as determined by carrying out electrophoresis on the glycoprotein and comparing its movement with marker proteins of known molecular weight. Experiments have shown that p185 forms dimers with other p185 molecules or with epidermal growth factor receptor (EGFR) and that these dimers exhibit elevated tyrosine kinase activity which brings about the transformed phenotype in cells having such dimers. Administration of nucleic acid molecules which encode proteins capable of forming dimers with other p185 molecules or with EGFR but which dimers do not exhibit elevated tyrosine kinase activity eliminate the transformed phenotype of neu-associated tumors in a population suffering from p185 mediated tumors. Further, administration of such nucleic acid molecules inhibit the neoplastic development in animals susceptible to developing neu transformed tumors.

The occurrence of mammalian tumors cells which express a translation product of the neu oncogene on their surfaces can be reversed or prevented by administration of nucleic acid molecules which comprise sequences that encode proteins which form dimers with p185 and/or EGFR but which do not have tyrosine kinase activity. In accordance with the invention, such nucleic acid molecules are provided in combination with delivery components, i.e. delivery vehicles, in order to facilitate incorporation of such nucleic acid molecules into the cells of an animal. An effective amount of such combinations are administered to an individual who is identified as suffering from or being susceptible to susceptible to neu-associated tumors.

The present invention provides nucleic acid molecules that have a nucleotide sequence which encodes a protein that lacks tyrosine kinase activity and dimerizes with human EGFR or human p185. The nucleic acid molecules are provided in combination with delivery components such that upon administration of the combination, the nucleic acid molecule is delivered to cells of the individual. When provided as a pharmaceutical composition, the combination is useful for the treatment of individuals suffering from p185 mediated cellular transformations. Such a pharmaceutical composition may also be useful for the prevention of p185 mediated cellular transformation, particularly in individuals susceptible to such transformation. The nucleic acid molecules of the invention may also be useful to produce specific p185 protein species in competent cells which may be subsequently isolated and used in various immunoassays to detect the presence of anti-p185 antibodies present in various bodily fluids.

According to one aspect of the invention, the nucleic acid molecule comprises a nucleic acid sequence that encodes a protein that lacks tyrosine kinase activity and dimerizes with human EGFR or human p185. The nucleic acid sequence may be either DNA or RNA. The nucleic acid sequence may encode any protein that dimerizes with human EGFR and/or p185 and which lacks tyrosine kinase activity. The nucleic acid sequence preferably encodes rat or human p185 species which may dimerize with human p185 or human EGFR and which also lacks tyrosine kinase activity.

In a preferred embodiment of the present invention, the nucleic acid sequence encodes truncation species of rat p185. The present invention includes any truncation species of rat p185 comprising either N-terminal or C-terminal deletions which dimerizes with either human p185 or human EGFR and which lacks tyrosine kinase activity. In addition, truncation species comprising substituted amino acids may also be effective. However, truncation species must be able to dimerize with human p185 or human EGFR. Thus, any portion of p185 that is able to dimerize with either human p185 or human EGFR while also having a tk$^-$ phenotype is included herein. Preferably, the nucleic acid sequence encodes a protein consisting of amino acid residues of rat p185 from about 1–690 to about 1–740.

In another preferred embodiment of the present invention, the nucleic acid sequence encodes species of rat p185 which lack tyrosine kinase activity by means of substitution or deletion of portions of amino acids, specifically those within the region of the molecule responsible for the tyrosine kinase activity. The present invention includes any tk⁻ species of rat p185, comprising either substitution or deletion of amino acids responsible for tk activity, wherein the species also dimerizes with human p185 or human EGFR. In addition, such species comprising substituted amino acids outside tk-associated sequences may also be effective.

Positions 753–758 of rat p185 comprise the critical lysine residue which directly binds the ATP molecule that is the phosphate donor in the tyrosine kinase reaction (Moller et al., *FEBS Lett.*, 1985, 186, 1; and Sternberg et al., *FEBS Lett.*, 1984, 175, 387 each of which is incorporated herein by reference). $Lys^{757}$ is 15 amino acid residues downstream of a conserved motif which is also found in nucleotide binding proteins without kinase activity (Wierenga et al., *Nature*, 1983, 302, 842 which is incorporated herein by reference). It is believed that the glycine residues form a hydrophobic pocket around the critical lysine residue which directly binds the ATP molecule (Moller et al., *FEBS Lett.*, 1985, 186, 1; and Sternberg et al., *FEBS Lett.*, 1984, 175, 387 each of which is incorporated herein by reference). Thus, any species of p185 which comprises a disruption in the ATP binding domain or surrounding region, wherein ATP no longer binds to the critical Lys residue, are included herein. However, these species must also dimerize with human p185 or human EGFR. Preferably, the nucleic acid sequence encodes a protein having the amino acid sequence of rat p185, which is set forth in GENEBANK Acession No. X03362, which is incorporated herein by reference, and Bargmann, et al. (1986) *Nature* 319, 226–230, MEDLINE Identifier:86118662; and Lofts, et al. (1993) *Oncogene* 8, 2813–2820; each of which is incorporated herein by reference, wherein this amino acid sequence contains a substitution or deletion, or any combination thereof, from about position 753 to about 758, wherein said substitution does not comprise a lysine residue.

In another preferred embodiment of the present invention, the nucleic acid sequence encodes rat p185 wherein the amino acid sequence contains a substitution or deletion at position 757. This substitution or deletion specifically removes the critical Lys residue at this position. Thus, ATP can no longer bind this molecule resulting in a tk⁻ phenotype.

In another preferred embodiment of the present invention, the nucleic acid sequence encodes truncation species of human p185. The present invention includes any truncation species of human p185 comprising either N-terminal or C-terminal deletions which dimerizes with either human p185 or human EGFR and which lacks tyrosine kinase activity. In addition, truncation species comprising substituted amino acids may also be effective. However, truncation species must be able to dimerize with human p185 or human EGFR. Thus, any portion of human p185 that is able to dimerize with either human p185 or human EGFR while also having a tk⁻ phenotype is included herein. Preferably, the nucleic acid sequence encodes a protein consisting of amino acid residues of human p185 from about 1–646 to about 1–704. In some embodiments, the nucleic acid sequence encodes a protein consisting of amino acid residues of human p185 from about 1–653.

In another preferred embodiment of the present invention, the nucleic acid sequence encodes species of human p185 which lack tyrosine kinase activity by means of substitution or deletion of portions of amino acids, specifically those within the region of the molecule responsible for the tyrosine kinase activity. The present invention includes any tk⁻ species of human p185, comprising either substitution or deletion of amino acids responsible for tk activity, wherein the species also dimerizes with human p185 or human EGFR. In addition, such species comprising substituted amino acids outside tk-associated sequences may also be effective.

Positions 749–754 of human p185 comprise the critical lysine residue which directly binds the ATP molecule that is the phosphate donor in the tyrosine kinase reaction. Any species of p185 which comprises a disruption in the ATP binding domain or surrounding region, wherein ATP no longer binds to the critical Lys residue, are included herein. However, these species must also dimerize with human p185 or human EGFR. Preferably, the nucleic acid sequence encodes a protein having the amino acid sequence of human p185, which is set forth in GENEBANK Acession No. X03363 which is incorporated herein by reference, and Yamamoto, et al. (1986) *Nature* 319, 230–234, MEDLINE identifier: 86118663, and Papewalls, et al. (1991) *Nucleic Acids Res.* 19, 5452–5452, MEDLINE Identifier: 92020265, each of which is incorporated herein by reference, wherein this amino acid sequence contains a substitution or deletion, or any combination thereof, from about position 749 to about 754, wherein said substitution does not comprise a lysine residue.

In another preferred embodiment of the present invention, the nucleic acid sequence encodes rat p185 wherein the amino acid sequence contains a substitution or deletion at position 753. This substitution or deletion specifically removes the critical Lys residue at this position. Thus, ATP can no longer bind this molecule resulting in a tk⁻ phenotype.

The above mentioned nucleic acid molecules are used in combination with a variety of delivery components, such as recombinant viral expression vectors or other suitable delivery means, so as to affect their introduction and expression in compatible host cells. In general, viral vectors may be DNA viruses such as recombinant adenoviruses and recombinant vaccinia viruses or RNA viruses such as recombinant retroviruses. Other recombinant vectors include recombinant prokaryotes which can infect cells and express recombinant genes. In addition to recombinant vectors, other delivery components are also contemplated such as encapsulation in liposomes, lipofectin-mediated transfection, transferrin-mediated transfection and other receptor-mediated means. The invention is intended to include such other forms of expression vectors and other suitable delivery means which serve equivalent functions and which become known in the art subsequently hereto.

In a preferred embodiment of the present invention, DNA is delivered to competent host cells by means of an adenovirus. One skilled in the art would readily understand this technique of delivering DNA to a host cell by such means. Although the invention preferably includes adenovirus, the invention is intended to include any virus which serves equivalent functions.

In another preferred embodiment of the present invention, RNA is delivered to competent host cells by means of a retrovirus. One skilled in the art would readily understand this technique of delivering RNA to a host cell by such means. Any retrovirus which serves to express the protein encoded by the RNA is intended to be included in the present invention.

In another preferred embodiment of the present invention, nucleic acid is delivered through folate receptor means. The nucleic acid sequence to be delivered to a host cell is linked to polylysine and the complex is delivered to the tumor cell by means of the folate receptor. U.S. Pat. No. 5,108,921 issued Apr. 28, 1992 to Low et al., which is incorporated herein by reference, describes such delivery components.

In another preferred embodiment of the present invention, nucleic acid is delivered through the use of lipofectin-mediated DNA transfer. LipofectAMINE™ liposome reagent (Life Technologies, Gaithersburg Md.) is a commerically availiable liposome encapsulation reagent which can be used for encapsulating cells following manufacturer's instructions. LipofectAMINIE™ liposome reagent encpasulated nucleic acid molecules may be delivered to a host cell using liposome formulation adminstration methods.

Pharmaceutical compositions according to the invention include delivery components in combination with nucleic acid molecules which further comprise a pharmaceutically acceptable carriers or vehicles, such as, for example, saline. Any medium may be used which allows for successful delivery of the nucleic acid. One skilled in the art would readily comprehend the multitude of pharmaceutically acceptable media that may be used in the present invention.

In some embodiments, the nucleic acid sequences encoding the various rat p185 species are constructed from c-neu cDNA according to the procedures set forth in the Examples. Nucleic acid sequences encoding wt, truncated, and mutated rat p185 species are thus prepared. The nucleotide sequences of the prepared p185 constructs are verified by DNA sequencing. One skilled in the art would readily understand methods of constructing such nucleic acid constructs.

After preparing such constructs, they are transfected into suitable host cells within which they are expressed. One skilled in the art would readily comprehend the vast number of suitable host cells from which to use. Within these suitable host cells, the ability of the p185 species, produced from the prepared nucleotide construct, to dimerize with either p185 or EGFR is examined. Such examination may include immunoblotting, flow cytometry, SDS-PAGE analysis, as well as other techniques that are well known to those skilled in the art. In addition, the tyrosine kinase activity of the p185 species may also be evaluated. It is also within the knowledge of one skilled in the art to evaluate tyrosine kinase activity by a variety of techniques.

Once the lack of tk⁻ phenotype of the p185 species is established and the ability to dimerize with either EGFR or p185 is established, the nucleic acid sequence encoding the p185 species may be subcloned into a suitable expression vector for transfection in human cells. Alternatively, the nucleic acid sequence may be used in combination with another delivery means as set forth above.

Another aspect of the present invention is a method of treating an individual suspected of undergoing cellular transformation by administering to the individual a pharmaceutical composition comprising a nucleic acid sequence in combination with delivery components, in an amount sufficient to reverse the transformation. The nucleic acid sequence encodes a protein that lacks tyrosine kinase activity and dimerizes with EGFR or p185. Individuals suffering from p185-associated tumors may be identified using well known techniques. Biopsies may be routinely performed and the presence of p185 on the tumor cells indicates a p185-assciated tumor.

Pharmaceutical compositions may be formulated by one having ordinary skill in the art with compositions selected depending upon the chosen mode of administration. Suitable pharmaceutical carriers are described in *Remington's Pharmaceutical Sciences,* A. Osol, a standard reference text in this field, which is incorporated herein by reference.

The pharmaceutical compositions of the present invention may be administered by any means that enables the active agent to reach the agent's site of action in the body of a mammal. Pharmaceutical compositions may be administered parenterally, i.e., intravenous, subcutaneous, intramuscular. Intravenous administration is the preferred route.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

The present invention is further illustrated by the following examples, which are not intended to be limiting in any way.

EXAMPLES

Example 1:
Construction of Mutants, Expression Vectors and Creation of Cell Lines Detailed methods for the construction of mutant p185 species, expression vectors and cell lines have been described previously (Qian et al., *Proc. Natl. Acad. Sci. U.S.A.,* 1994, 91, 1500; and Weiner et al., *Oncogene,* 1989, 4, 1175, each of which is incorporated herein by reference).

Construction of mutant N757

The ATP-binding mutant Nneu K757M (N757) was derived from pSV2TneuK757M (Weiner et al., *Oncogene,* 1989, 4, 1175, which is incorporated herein by reference) by subcloning techniques. This construct was prepared by site-directed mutagenesis to substitute a Met for Lys$^{757}$. One skilled in the art would readily understand the preparation of a such a mutant by site-directed mutagenesis. Briefly, an XbaI fragment of pSV2neuT corresponding to a 1.2 kb band spanning the probable ATP binding site of the published nucleotide sequence was cloned into M13Mp18 and transfected into *E. coli* strain CJ236 (dot⁻, ung⁻) pUC13 so that the HindIII site of the polylinker fell at the 5' end of the inserted sequences. Mutagenesis was performed as described utilizing a primer in which the codon AAG, coding for Lys, was replaced by the codon AUG corresponding to Met (Bargmann et al., *Nature,* 1986, 319, 226, which is incorporated herein by reference). The point mutations thus created were verified by DNA sequencing. The plasmid bearing the novel mutation was cleaved with XbaI which liberated the original fragment. This fragment was isolated by standard techniques known to those skilled in the art and ligated back into pSV2-neu to regenerate the oncogenic p185neu expression vector except that the vector contained the substitution of Met for Lys at amino acid position 757 (clone M757).

Construction of mutant N691stop

The carboxy-terminal 591 amino acid deletion mutant N691stop was derived from pSV2Nneu (Bargmann et al., *Nature,* 1986, 319, 226, which is incorporated herein by reference) by substitution of a stop codon for normal codon Thr$^{691}$ via site-directed mutagenesis.

Construction of Ndx

The carboxy-terminal 541 amino acid deletion mutant Ndx was derived from c-neu cDNA by the deletion of an XbaI fragment and insertion of a stop codon for the normal codon at position 741 via site-directed mutagenesis.

Construction of expression vectors

For expression vectors, fragments containing mouse dihydrofolate reductase (DHFR) cDNA from pSV2DHFR and bacterial neomycin phosphotransferase-resistant gene (neo$^r$) from pSV2NEO (Southern et al., *J. Mol. Appl. Genet.*, 1982, 1, 327, which is incorporated herein by reference) were subcloned into pSV2Nneu so that a 14.8 kb DHFR, neo$^r$, and Nneu cDNA combined vector was generated. The wt or mutated neu fragments were isolated and ligated back into a pSV2neo$^r$/dhfr/Nneu expression vector. All these cDNAs were under the control of the simian virus 40 (SV40) early promoter. A gene unit encoding the bacterial hygromycin-resistance (Hyg$^r$) gene under the control of herpes simplex virus thymidine kinase promoter was isolated from pHyg and substituted for a neo$^r$ gene fragment in pEGFR1 (Gorman et al., *J. Cell. Biochem.*, 1988, 12A, Suppl., C219, which is incorporated herein by reference) to generate another combined expression vector, pEGFR/Hyg$^r$. Human EGFR cDNA was under the control of the SRα promoter, an efficient transcriptional control element containing SV40 early promoter and the R-U5 segment of human T-cell leukemia virus type 1 long terminal repeat (Takebe et al., *Mol. Cell. Biol.*, 1988, 8, 466, which is incorporated herein by reference).

Transfection and maintenance of cell lines

The construct pEGFR/Hyg$^r$ was first transfected into NR6 cells (Pruss et al., *Proc. Natl. Acad. Sci. U.S.A.*, 1977, 74, 3918, which is incorporated herein by reference) by calcium phosphate precipitation. After 3 weeks of hygromycin selection (35 μg/ml), the EGFR expression of resultant colonies was identified by anti-EGFR immunoblotting. Cells that expressed EGFR were further cloned by limiting dilution prior to second round transfection with neu cDNA expression vectors. The EGFR-expressing cells, named NE91, together with NR6 cells, were transfected with pSV2neo$^r$/dhfr/neu encoding wt or mutant neu proteins and selected with G418. The Neu-expressing clones in NR6 cells and NE91 cells were screened by flow cytometric assay with anti-neu monoclonal antibody 7.16.4 staining (Drebin et al., *Cell*, 1985, 41, 695, which is incorporated herein by reference) and were named NR6 Neu and NE Neu, respectively. These DHFR-containing single (expressing Neu only) or double (expressing Neu and EGFR) transfected clones were maintained in Dulbecco's modified Eagle's medium (DMEM) containing 5% fetal bovine serum, G418 (0.3 mg/ml), and hygromycin (15 μg/ml). Neu amplification was achieved by stepwise increased dosages (0.3–1.0 μM) of methotrexate for a few months in order to elevate receptor expression level.

Flow cytometry

Cells were removed from tissue culture dishes with buffered EDTA (Versene, M. A. Bioproducts) and washed twice in FACS medium (Hanks' balanced salt solution (Gibco) supplemented with 2% fetal calf serum, 0.2% sodium azide, and 10 mM HEPES). 1×10$^6$ cells were incubated in 0.1 ml of FACS medium with 7.16.4, anti-neu monoclonal antibody (Drebin et al., *Cell*, 1985, 41, 695, which is incorporated herein by reference) or isotype matched irrelevant control antibody for 1 hour at 4° C. The cells were washed twice with 2.5 ml of FACS medium. The cell pellet was resuspended and cells were incubated with 0.1 ml of FITC-conjugated goat rabbit anti-mouse IgG (reactive with antibody heavy and light chains, Tago) diluted 1:50 in FACS medium, for 1 hour at 4° C. Cells were washed twice and analyzed on a FACS IV Becton Dickenson.

Example 2:

Tyrosine Kinase Activity

Membrane purification

Cells were lysed by a combination of snap freeze-thawing and Dounce homogenization as described in Gaulton et al., *J. Immunol.*, 1986, 7, 2470, which is incorporated herein by reference. The nuclear fraction was removed by centrifugation at 2000×g for 5 minutes. The 2000×g supernatant fraction was then recentrifuged at 25000×g for 30 minutes at 4° C., and the 25000×g supernatant was retained as the cytosol fraction. The pellet was redissolved in 1.5 ml of membrane buffer (40 mM NaCl, 0.1 mM EDTA, 20 mM HEPES (pH 6.8), 2 mM PMSF, and 5 mM Na pyrophosphate) then layered over a (20%–37%) sucrose solution in membrane buffer and centrifuged at 22000 rpm for 18 hours at 2° C. by using a Beckman SW50.1 rotor. The membrane-rich interface was removed in 1 ml total volume, diluted with 10 ml of membrane buffer, and was recentrifuged at 40000 rpm for 60 minutes by using an SW40.1 rotor exactly as described in Zick et al., *Biochem. Biophys. Res. Commun.*, 1984, 119, 6, which is incorporated herein by reference. The resultant pellet containing purified membrane fragments, was redissolved in 100 μl of Kinase buffer (see below) per 10$^7$ original cells. Membrane proteins were quantitated using a BioRad protein assay kit and stored at −80° C. until assay.

Tyrosine kinase activity in membranes

Membrane concentrations were determined by the method of Bradford as described in Gaulton et al., *J. Immunol.*, 1986, 7, 2470, which is incorporated herein by reference. Dilutions of membranes were incubated in quadruplicate in the presence or absence of synthetic polypeptide containing tyrosine as a specific indicator of tyrosine phosphorylation. Kinase reaction buffer, (50 μl of 0.1M Hepes pH 7.3, 10 mM MgCl$_2$, 5 mM MnCl$_2$, 50 μM Na$_3$VO$_4$ were incubated in the presence of ATP (1 μCi of gamma [$^{32}$P]ATP; Amersham) for 5 minutes at room temperature. Reactions were halted by adding 5 mM EDTA (final concentration) followed immediately by TCA immunoprecipitation onto glass fiber filters (Whatman GF/A). Filters were washed extensively with TCA followed by ether, air-dried, immersed in scintillation cocktail (Biofluor) and beta emissions determined. Quadruplicate wells assayed in the absence of tyrosine containing substrate were subtracted from tyrosine substrate containing wells.

Membrane proteins were incubated with the random polymer of glutamic acid-tyrosine (4:1) poly glu:tyr, PGT) as substrate for tyrosine phosphorylation as described in Zick et al., *Biochem. Biophys. Res. Commun.*, 1984, 119, 6, which is incorporated herein by reference. Briefly, membrane proteins were incubated in 50 μl of 10 mM HEPES pH 7.2, containing 10 mM MgCl$_2$, 100 μM Na$_3$VO$_4$, and 150 μM (10 μCi) [$^{32}$P]ATP for 15 minutes at room temperature in the presence (specific) or absence (background) of poly glu:tyr substrate at 2.5 mg/ml. Reactions were stopped by the addition of EDTA to 50 mM final concentration and cold excess ATP and samples were spotted onto Whatman glass fiber filter paper. Filters were washed 3 times with ice cold 10% TCA containing 10 mM pyrophosphate and 1 mM ATP followed by once with acetate. Samples were then dried and counted in BioFlur (NEN). For immunoprecipitation of phosphotyrosine containing membrane proteins, 50 μg of purified membranes were incubated in kinase buffer as described above for 15 minutes. After labeling, samples were solubilized in Lysis buffer supplemented with 5 mM EDTA, precleared and immune precipitated with 2 μl ascites from MA-2G8A6+protein A agarose. The MA-2G8 antibody specifically precipitates phosphotyrosine labeled polypeptides as described in Daniel et al., *Proc. Natl. Acad. Sci. U.S.A.*, 1985, 82, 2084, which is incorporated herein by reference.

Example 3:
Dimerization with p185 or EGFR

EGFR and p185 heterodimers are detected by anti-receptor-specific antibody immunoprecipitation and immunoblotting after EGF and chemical cross-linker treatment. The physical association of EGFR and kinase-deficient p185 proteins were examined in this manner.

Chemical cross-linking assay

Cells were cultured overnight in 10 cm Petri dishes, incubated with or without EGF (GIBCO/BRL) at 37° C. for 10–15 minutes, and washed twice with cold phosphate buffered saline (PBS). Three ml of PBS containing 2 mM bis(sulfosuccinimidyl) suberate ($BS^3$) or 3,3'-dithiobis(sulfosuccinimidylpropionate) (DTSSP) (Pierce) was added and incubated at 18° C. for 30 minutes with occasional rocking of the plates. After quenching the crosslinking reaction mixture with buffer containing 10 mM Tris-HCl, 0.9% NaCl, and 0.1M glycine, cells were washed twice with cold PBS and solubilized with PI/RIPA buffer (Wada et al., *Cell*, 1990, 61, 1339, which is incorporated herein by reference).

Labeling and immunoprecipitation

All reagents were obtained from Sigma unless otherwise indicated. For [$^{32}$P]-labeling $1 \times 10^6$ cells were plated and were cultured for 24 hours and then were incubated with inorganic [$^{32}$p] (Amersham) at 0.5 mCi/ml in 5% FCS/phosphate-free RPMI for 6 hours. After labeling cells were washed with cold phosphate buffered saline containing 400 $\mu$M EDTA, 10 mM sodium fluoride, 10 mM sodium pyrophosphate and 400 $\mu$M sodium orthovanadate and were lysed in lysis buffer (1% NP40, 0.1% deoxycholate, 0.1% SDS, 0.15M NaCl, 0.01M sodium phosphate pH 7.4, 1% Trasylol, 1 mM PMSF, 2 mM EDTA, 10 mM sodium fluoride, 10 mM sodium pyrophosphate, 400 $\mu$M $Na_3VO_4$, 10 mM iodoacetoamide and 1 mM ATP) for 30 minutes. Pre-cleared supernatants were subjected to immunoprecipitation with monoclonal antibody 7.16.4, or rabbit antisera recognizing human and rat neu proteins DBW-2 (Kokai et al., *Proc. Natl. Acad. Sci. U.S.A.*, 1988, 84 8498, which is incorporated herein by reference). Immunoprecipitates were boiled in Laemmli's sample buffer and analyzed in 8% SDS-PAGE (Laemmli, *Nature*, 1970, 227, 680, which is incorporated herein by reference). Dried gels were exposed to prefogged film at −70° C. Densitometer tracings of gels were performed on a Hoefer GS300 scanning densitometer. Relative densities were determined by cutting out in side by side experiments the relevant scanned peaks and weighing them on an analytical balance. The incorporation of the proto oncogenic and oncogenic p185neu was then directly compared.

Focus formation and tumorigenicity assays

Cells ($10^4$) were plated in Petri dishes and cultured in DMEM containing 2% FBS. The medium was changed every 3–4 days. After 3 weeks in culture, cells were fixed with 10% formalin and stained with hematoxylin to observe morphologically transformed foci. To analyze the tumor growth in athymic nude mice, cells ($10^6$) of each line were suspended in 0.1 ml of PBS and injected intradermally in the mid-dorsum of NCR nude mice. PBS alone was also injected as a control. Tumor growth was monitored every 4–5 days up to 10–12 weeks.

RESULTS

NE91 is a transfected cell line expressing the EGFR in NR6 cells (Pruss et al., *Proc. Natl. Acad. Sci. U.S.A.*, 1977, 74, 3918, which is incorporated herein by reference), a mouse fibroblast cell line devoid of endogenous EGFR. Wildtype (WT) cellular p185 (Nneu) or kinase deficient Neu (i.e. N757 and N691stop, carrying a point mutation K757M at the ATP-binding site and cytoplasmic domain deletion, respectively), were expressed in both NR6 and NE91 cells. The resultant transfected clones were named NR6 Neu or NE Neu, respectively.

Kinase deficient mutant neu proteins suppressed EGFR function in cellular transformation and abolished the transforming synergy with EGFR We have previously shown that co-expression of increased levels of EGFR and cellular p185, but not either separately, transformed murine fibroblast cells completely as demonstrated with the M1 cell line (Kokai et al., *Cell*, 1989, 58, 287, which is incorporated herein by reference). In the present study, the transformed phenotypes of these transfected cells expressing WT or kinase deficient Neu proteins in the presence or absence of EGF were analyzed.

NE91 cells expressing EGFR alone formed a monolayer in the absence of EGF and foci in the presence of EGF. The observed incomplete transformation, (i.e., in an EGF-dependent manner), is in agreement with previous reports (DiFiore et al., *Cell*, 1987, 51, 1063; Dobashi et al., *Proc. Natl. Acad. Sci. U.S.A.*, 1991, 88, 8582, each of which is incorporated herein by reference). However, in a similar manner to M1 cells, co-expression of WT cellular p185 and EGFR in NE NneuB2 cells resulted in complete transformation, i.e., the focus formation was EGF-independent. Cell lines co-expressing EGFR with either form of kinase deficient Neu (NE N757 and NE N691stop cells) did not form foci even in the presence of EGF. Similar results were observed when anchorage-independent colony growth in soft agar was assayed.

Tumor growth in nude mice was used as a criterion for complete transformation in vivo. B104-1-1 cells expressing oncogenic p185 were used as a positive control and tumors caused by those cells appeared quickly (with a latency of 5 days). Cell lines expressing equivalent levels of EGFR (NE91) or cellular p185 (NR6 Nneu) alone did not grow tumors. However, injection of the cells co-expressing both EGFR and cellular p185 (M1 and NE NneuB2) caused tumors (2–3 weeks latency). The results were consistent with a previous report (Kokai et al., *Cell*, 1989, 58, 287, which is incorporated herein by reference).

However, no tumors were observed (>10 weeks) after injection of cell lines expressing kinase deficient Neu alone or co-expressed with EGFR. These data suggested that the normal cellular p185 kinase activity and EGFR function was required for synergistic transformation and tumor formation. Co-expression of kinase deficient Neu proteins with EGFR not only abolished this type of synergy, but also suppressed the EGF-dependent transformation potential of EGFR. Therefore, EGF receptor function mediated by ligand stimulation was further analyzed in the following studies.

EGF-induced receptor down-regulation was less efficient in neu kinase deficient mutant cells We next examined whether normal receptor down-regulation was affected by co-expression with kinase deficient Neu. Cells were incubated with EGF for various times prior to cell surface staining with anti-neu mAb 7.16.4 or anti-EGFR mAb 425 followed by the staining with FITC conjugated anti-mouse-IgG. The cell surface expression of either receptor was analyzed using flow cytometric analysis. The cell surface expression of EGFR in NE91 cells was reduced after 15 minutes of EGF treatment and over 60% of receptors disappeared from the cell surface after 1 hour treatment. The efficiency of EGFR down-regulation in M1 cells (co-expressing WT Neu and EGFR) was similar to that observed in NE91 cells. About 20% of cellular p185 co-downregulated along with EGFR in M1 cells. Similar results were observed in NE Nneu B2 cells. However, cell lines expressing cellular p185 only did not respond to EGF. In cell lines in which EGFR was co-expressed with kinase deficient mutant Neu proteins the down-regulation of EGFR was less efficient (maximum reduction was about 20–25%). In addition, the surface expression of either mutant Neu protein was not altered significantly in these cells upon EGF treatment.

Increased receptor half-lives observed in kinase deficient mutant neu co-expressed cells To determine whether the receptors that were down-regulated from the cell surface underwent degradation, pulse-chase labeling of receptor proteins was performed as described in materials and methods, and immunoprecipitated Neu and EGFR proteins were analyzed by SDS-PAGE. EGF treatment caused a rapid degradation of EGFR in NE91 cells (expressing EGFR alone). A similar EGFR degradation rate was observed in M1 cells upon EGF treatment. However, EGF-induced EGFR degradation was slowed in cells co-expressing EGFR with either form of Neu kinase deficient mutant (NE N757 or NE N691 stop).

The degradation patterns of WT or mutant Neu proteins in response to EGF treatment were also investigated. The labeled WT cellular p185 in both M1 cells and NE NneuB2 cells disappeared proportionately to the time treated with EGF, indicating that WT cellular p185 is efficiently co-degraded with EGFR. There was only a slight reduction of N757 protein levels and no discernible change in the abundance of the truncated N691stop protein after EGF treatment up to 6 hours. The suggested normal half-life of human c-erbB2 in mammary epithelial cells is 11–13 hours (Kornilova et al., *Oncogene*, 1992, 7, 511, which is incorporated herein by reference). Densitometric analysis of our autoradiograms confirmed that the half life of WT cellular p185 was reduced to 3–4 hours after EGF treatment, while the mutant Neu levels did not change significantly over the time course examined.

EGF binding affinity in wt or mutant neu protein expressed cells

Our experiments have demonstrated that kinase deficient Neu mutants suppress EGFR functions, such as kinase activity (Qian et al., *Proc. Natl. Acad. Sci. U.S.A.*, 1994, 91, 1500, which is incorporated herein by reference), EGF-mediated transformation, receptor down-regulation and degradation. Since these effects could be interpreted, in part, by altered EGF binding affinities, we analyzed [$^{125}$I]-EGF binding parameters by Scatchard analysis.

The mean dissociation constants (Kd) of [$^{125}$I]-EGF binding to these cell lines were determined from three individual experiments. EGFR in NE91 cells displayed two binding components representing high ($7.5 \times 10^{-11}$M) and low ($4.4 \times 10^{-9}$M) binding affinities, and the fraction of high affinity receptors was 5.4% of the total receptors. Co-expression of EGFR with WT Neu in NE NneuB2 cells resulted in a slight increase in EGF binding affinities ($3.2 \times 10^{-11}$M) and ($2.0 \times 10^{-9}$M) for both high and low affinity subclasses, respectively, and the fraction of high affinity receptors was 5.7%. The increased affinities for M1 cells were reproducible and the Kd values ($1.3 \times 10^{-11}$M and $1.8 \times 10^{-9}$M) were in agreement with our previous reports, Kokai et al., *Cell*, 1989, 58, 287; and Wada et al., *Cell*, 1990, 61, 1339, each of which is incorporated herein by reference). However, the EGFR in kinase deficient Neu co-expressing cells displayed predominantly low affinity EGF binding, $4.9 \times 10^{-9}$M and $5.2 \times 10^{-9}$M in NE N691 and NE N757 cells, respectively, although a rare high affinity subclass of EGFR was sometimes detectable, i.e., $7.2 \times 10^{-11}$M (0.5%) in NE N691stopcells and $6.6 \times 10^{-11}$M ($\leq 1\%$) in NE N757 cells. These rare species may represent a set of EGFR homodimers still observed when co-expressed with kinase inactive Neu proteins (Qian et al., *Proc. Natl. Acad. Sci. U.S.A.*, 1994, 91, 1500, which is incorporated herein by reference). It is clear from the Scatchard analysis that EGFR in cells co-expressing kinase active WT Neu display the normal percentage of high affinity EGF receptors, with a slightly increased affinity for EGF when compared with NE91 cells. However, the co-expression of kinase deficient Neu protein greatly reduced the EGF-binding affinities in correlation with the reduced heterodimeric kinase activities.

DISCUSSION

In the current studies, receptor functions and cell phenotypes have been analyzed by using stably transfected cell lines co-expressing EGFR with WT or mutant Neu proteins. Unlike WT Neu, the kinase deficient Neu did not cooperate with EGFR to mediate cell transformation; in addition, we have shown novel aspects of dominant negative receptor functions resulting from the interaction of mutant Neu with EGFR.

The intermolecular association and resultant tyrosine kinase activation between EGFR and WT (Qian et al., *Proc. Natl. Acad. Sci. U.S.A.*, 1992, 89, 1330, which is incorporated herein by reference) or mutant Neu proteins (Qian et al., *Proc. Natl. Acad. Sci. U.S.A.*, 1994, 91, 1500, which is incorporated herein by reference) have been well-characterized: our studies showed that heterodimerization of EGFR and c-neu products can be detected even in the absence of EGF, and are favored over either form of homodimerization. However, the homodimerization and co-dimerization of WT EGFR and cytoplasmic domain deleted EGFR were equally efficient and EGF-dependent (Kashles et al., *Mol. Cell Biol.*, 1991, 11, 1454, which is incorporated herein by reference). The predominance of heterodimers may help to explain the resultant cell phenotypes, and inducible dominant negative effect of kinase deficient Neu on suppression of EGFR function, which occurred significantly even when there is a 1:1 ratio of EGFR and mutant Neu proteins.

Receptor interaction with resultant activation of the tyrosine kinase occurs by an intermolecular mechanism and is often followed by rapid transphorylation events as has been observed in pp60$^{c-src}$ (Cooper et al., *Proc. Natl. Acad. Sci. U.S.A.*, 1988, 85, 4232, which is incorporated herein by reference), insulin receptor (Boni-Schnetzler et al., *J. Biol. Chem.*, 1988, 263, 6822, which is incorporated herein by reference) and EGFR (Honegger et al., *Mol. Cell. Biol.*, 1990, 10, 4035, which is incorporated herein by reference). Transphosphorylation also occurs between hetero-receptor species, EGFR and Neu/c-erbB2 (Connelly et al., *Proc. Natl. Acad. Sci. U.S.A.*, 1990, 87, 6054; Spivak-Kroizman et al., *J. Biol. Chem.*, 1992, 267, 8056; and Qian et al., *Proc. Natl. Acad. Sci. U.S.A.*, 1994, 91, 1500; each of which is incorporated herein by reference). Preferential heterodimerization of EGFR and Neu receptor (Qian et al., *Proc. Natl. Acad. Sci. U.S.A.*, 1994, 91, 1500, which is incorporated herein by reference) may facilitate transphosphorylation of N757 by EGFR. Currently, the specific substrates for the EGFR and Neu kinase have not been well-characterized. In vitro binding assays showed that the phosphorylated kinase deficient N757 was still able to associate with recombinant SH2-containing protein upon EGF-treatment. However, unlike active heterodimers in M1 and NE NneuB2 cells, the loss of Neu kinase activity of mutant heterodimer of NE N757 cells may prohibit the phosphorylation of certain cellular substrates. Furthermore, the predominant trans-phosphorylation of N757 by EGFR and the occupancy of cellular substrates in nonfunctional N757 may compete with EGFR for cellular signaling molecules leading to qualitative and quantitative reductions in EGFR function. Therefore, the defective heterodimer may not transmit signals as effectively as the kinase active heterodimer and EGFR homodimer, thus impairing the synergistic signaling that lead to cell transformation seen in M1 and NE NneuB2 cells and inhibiting EGFR function. Studies of heterodimerization of EGFR with cytoplasmic domain deleted N691stop showed that the heterodimer form was inactive due to the failure of protein-protein interaction between the cytoplasmic domains, indicating that Neu/c-erbB2 is not simply a substrate for EGFR, but a trans-activator for EGFR as well (Qian et al., *Proc. Natl. Acad. Sci. U.S.A.,* 1994, 91, 1500, which is incorporated herein by reference). Thus, the reduced amounts of normal EGFR homodimer form and the preponderance of unproductive heterodimers resulted in the suppression of normal EGFR function and resultant dominant negative phenotype. The observation is comparable to the effects of dimers formed between WT EGFR and cytoplasmic domain deleted EGFR (Kashles et al., *MOl. Cell. Biol.,* 1991, 11, 1454, which is incorporated herein by reference).

Kinase active receptors have been reported to be targeted to lysosomes for degradation upon ligand binding (Chen et al., *Cell,* 1989, 59, 33; Felder et al., *Cell,* 1990, 61, 623, which is incorporated herein by reference). Previous studies using kinase-deficient insulin receptors (McClain et al., *J. Biol. Chem.,* 1987, 262, 14663; and Russell et al., *J. Biol. Chem.,* 1987, 262, 11833; each of which is incorporated herein by reference) and EGFR (Honegger et al., *Cell,* 1987, 51, 199, which is incorporated herein by reference) suggested that active kinase domains are essential for normal ligand-induced receptor routing. We used EGF-treated cell lines to study how the activities of receptor kinase complexes correlate with receptor endocytosis and destruction. Our work demonstrates that EGFR is WT Neu co-expressed cells (M1 or NE NneuB2) undergoes rapid down-regulation and degradation upon EGF stimulation. This process was significantly retarded in mutant cells compared to the NE91 cells expressing EGFR alone. Only the WT cellular p185, but not the kinase deficient mutant Neu protein, was co-downregulated and co-degraded with EGFR. Similarly, EGF-treatment of the human mammary cell line HC11 cells affected c-erbB2 protein surface expression and protein turnover: a 3–4 fold increase in the lysosomal c-erbB2 protein and the half-life of c-erbB2 proteins was reduced from 11 hour (untreated) to 3.5 hour (EGF-treated) (Kornilova et al., *Oncogene,* 1992, 7, 511, which is incorporated herein by reference). Together with our observation, these results suggested that WT Neu/c-erbB2, (but not kinase deficient Neu), associates with EGFR and an active receptor tyrosine kinase complex and undergoes normal receptor routing.

In conclusion, our results provide experimental evidence that the defective or inactive heterodimers of EGFR and kinase deficient Neu proteins impair synergistic hetero-receptor signaling, suppress the function of normal EGFR, and abolish the transformed phenotype in living cells. Our experimental model suggests a causal relationship between heterodimeric kinase activities and cell malignancy which may have clinical implications. A recent report has shown that a truncated ecto-domain of c-erbB2 protein produced by alternative RNA processing in human carcinoma cells over-expressing $p185^{c-erbB2}$ receptor results in resistance to the growth inhibiting effects of the anti-c-erbB2 monoclonal antibody (Scott et al., *Mol. Cell. Biol.,* 1993, 13, 2247, which is incorporated herein by reference). It is speculated that the direct gene transfer of kinase deficient Neu cDNA into tumor cell lines with co-overexpression of EGFR and Neu/c-erbB2 may relieve the malignant phenotype, as the mutant Neu proteins may suppress the function of either normal EGFR or c-erbB2 receptors by homo- or hetero-receptor interactions.

What is claimed is:

1. A nucleic acid molecule that comprises a nucleotide sequence that encodes a protein that can form a dimer with epidermal growth factor receptor, and can form a dimer with p185, wherein said protein lacks tyrosine kinase activity.

2. A nucleic acid molecule that comprises a nucleotide sequence that encodes a protein that can form a dimer with epidermal growth factor receptor, and can form a dimer with p185, wherein said protein lacks tyrosine kinase activity; and wherein said nucleic acid molecule comprises a nucleotide sequence that encodes a protein selected from the group consisting of:

a protein consisting of amino acid residues from about 1–690 to about 1–740 of rat p185;

a protein consisting of amino acid residues from about 1–646 to about 1–704 of human p185;

a protein having the amino acid identical to rat p185 except having a substitution or deletion of one or more amino acid residues from about amino acid position 753 to about 758, wherein said substitution does not comprise a lysine residue;

a protein having an amino acid sequence identical to human p185 except having a substitution or deletion of one or more amino acid residues from about amino acid position 749 to about 754, wherein said substitution does not comprise a lysine residue;

a protein having an amino acid sequence identical to rat p185 except having a substitution or deletion at amino acid position 757; and a protein having an amino acid sequence identical to human p185 except having a substitution or deletion at amino acid position 753.

3. The nucleic acid molecule of claim 2 wherein said nucleic acid molecule comprises a nucleotide sequence that encodes a protein selected from the group consisting of:

a protein consisting of amino acid residues from about 1–690 to about 1–740 of rat p185;

a protein having the amino acid identical to rat p185 except having a substitution or deletion of one or more amino acid residues from about amino acid position 753 to about 758, wherein said substitution does not comprise a lysine residue; and a protein having an amino acid sequence identical to rat p185 except having a substitution or deletion at amino acid position 757.

4. The nucleic acid molecule of claim 2 wherein said nucleic acid molecule comprises a nucleotide sequence that encodes a protein selected from the group consisting of:

a protein consisting of amino acid residues from about 1–646 to about 1–704 of human p185;

a protein having an amino acid sequence identical to human p185 except having a substitution or deletion of one or more amino acid residues from about amino acid position 749 to about 754, wherein said substitution does not comprise a lysine residue; and a protein having an amino acid sequence identical to human p185 except having a substitution or deletion at amino acid position 753.

5. The nucleic acid molecule of claim 2 in combination with a delivery vehicle for delivering said nucleic acid molecule to a cell.

6. The nucleic acid molecule of claim 2 wherein said nucleic acid molecule is an RNA molecule which is a retroviral genome.

7. The nucleic acid molecule of claim 2 wherein said nucleic acid molecule is a DNA molecule which is an adenovirus genome or vaccinia virus genome.

8. The nucleic acid molecule of claim 2 wherein said nucleic acid molecule is a DNA molecule in combination with a folic acid receptor ligand.

9. A recombinant virus comprising a viral genome comprising a nucleic acid molecule according to claim 1.

10. The recombinant virus of claim 9 wherein said recombinant virus is a recombinant adenovirus.

11. The recombinant virus of claim 9 wherein said recombinant virus is a recombinant retrovirus.

12. The nucleic acid molecule of claim 2 wherein said nucleic acid molecule comprises a nucleotide sequence that encodes a protein selected from the group consisting of:

a protein consisting of amino acid residues from 1–690 to 1–740 of rat p185;

a protein having the amino acid identical to rat p185 except having a substitution or deletion of one or more amino acid residues from amino acid position 753 to 758, wherein said substitution does not comprise a lysine residue; and a protein having an amino acid sequence identical to rat p185 except having a substitution or deletion at amino acid position 757.

13. The nucleic acid molecule of claim 2 wherein said nucleic acid molecule comprises a nucleotide sequence that encodes a protein selected from the group consisting of:

a protein consisting of amino acid residues from about 1–646 to about 1–704 of human p185;

a protein having an amino acid sequence identical to human p185 except having a substitution or deletion of one or more amino acid residues from about amino acid position 749 to about 754, wherein said substitution does not comprise a lysine residue; and a protein having an amino acid sequence identical to human p185 except having a substitution or deletion at amino acid position 753.

14. A recombinant virus comprising a nucleic acid molecule of claim 3.

15. The recombinant virus of claim 14 wherein said recombinant virus is a recombinant adenovirus.

16. The recombinant virus of claim 14 wherein said recombinant virus is a recombinant retrovirus.

17. A recombinant virus comprising the nucleic acid molecule of claim 4.

18. The recombinant virus of claim 17 wherein said recombinant virus is a recombinant adenovirus.

19. The recombinant virus of claim 17 wherein said recombinant virus is a recombinant retrovirus.

20. A nucleic acid molecule that comprises a nucleotide sequence that encodes a mutated and/or truncated p185 protein that
  a) can form a dimer with epidermal growth factor receptor,
  b) can form a dimer with p185, and
  c) lacks tyrosine kinase activity.

21. The nucleic acid molecule of claim 20 wherein said mutated and/or truncated p185 protein is a mutated and/or truncated human p185 protein.

22. The nucleic acid molecule of claim 20 wherein said mutated and/or truncated p185 protein is a mutated and/or truncated rat p185 protein.

23. The nucleic acid molecule of claim 20 wherein said protein is a mutated p185 protein which contains deletions and/or substitutions in the cytoplasmic domain.

24. The nucleic acid molecule of claim 20 wherein said protein is a truncated p185 protein is a truncated p185 molecule having an incomplete cytoplasmic domain.

25. The nucleic acid molecule of claim 20 wherein said protein is a mutated p185 protein which contains deletions and/or substitutions in the cytoplasmic domain.

26. The nucleic acid molecule of claim 20 in combination with a delivery vehicle for delivering said nucleic acid molecule to a cell.

27. A recombinant virus comprising a viral genome comprising a nucleic acid molecule according to claim 20.

28. The recombinant virus of claim 27 wherein said recombinant virus is a recombinant adenovirus.

29. The recombinant virus of claim 27 wherein said recombinant virus is a recombinant retrovirus.

* * * * *